US 8,553,842 B2

(12) United States Patent
Moon et al.

(10) Patent No.: US 8,553,842 B2
(45) Date of Patent: Oct. 8, 2013

(54) X-RAY APPARATUS AND CONTROL METHOD THEREOF

(75) Inventors: Kyung Won Moon, Seongnam-si (KR); San Lim, Suwon-si (KR); Kwang Kyu Lee, Yongin-si (KR); Kyung Shik Roh, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 134 days.

(21) Appl. No.: 13/137,634

(22) Filed: Aug. 30, 2011

(65) Prior Publication Data

US 2012/0087479 A1    Apr. 12, 2012

(30) Foreign Application Priority Data

Oct. 8, 2010    (KR) .................. 10-2010-0098312

(51) Int. Cl.
*H05G 1/08* (2006.01)
*H05G 1/02* (2006.01)

(52) U.S. Cl.
USPC .......................................... 378/115; 378/197

(58) Field of Classification Search
USPC .................. 378/114, 115, 196–198
See application file for complete search history.

(56) References Cited

U.S. PATENT DOCUMENTS

| 4,107,590 | A | * | 8/1978 | Pury et al. ............. 318/628 |
| 4,163,929 | A | * | 8/1979 | Janu et al. ............. 318/628 |
| 4,674,107 | A | * | 6/1987 | Urban et al. ............ 378/98 |
| 4,697,661 | A | * | 10/1987 | Pajerski et al. ........ 180/6.5 |
| 5,351,282 | A | * | 9/1994 | Kadowaki et al. ...... 378/198 |
| 5,416,819 | A | * | 5/1995 | Uzuyama et al. ....... 378/116 |
| 5,768,336 | A | * | 6/1998 | Khutoryansky et al. ... 378/116 |
| 6,422,747 | B2 | * | 7/2002 | Akutsu et al. ......... 378/198 |
| 6,871,715 | B1 | * | 3/2005 | Diaz Carmena et al. .. 180/65.51 |
| 7,177,393 | B2 | * | 2/2007 | Kanemitsu ............ 378/117 |
| 7,597,473 | B2 | * | 10/2009 | Graumann et al. ...... 378/197 |
| 8,201,999 | B2 | * | 6/2012 | Uchida et al. .......... 378/197 |
| 2010/0243924 | A1 | * | 9/2010 | Uchida et al. .......... 250/522.1 |
| 2012/0087479 | A1 | * | 4/2012 | Moon et al. ............ 378/189 |
| 2012/0087480 | A1 | * | 4/2012 | Yang et al. ............ 378/197 |

* cited by examiner

*Primary Examiner* — Thomas R Artman
(74) *Attorney, Agent, or Firm* — Staas & Halsey LLP

(57) ABSTRACT

An X-ray apparatus includes guide rails arranged along different axes, an X-ray tube movably mounted on at least one of the guide rails and adapted to be moved upon user force, motors provided at the guide rails to move the X-ray tube, a force detection unit to detect the user force, and a control unit to determine a direction of force and drive the motor provided at the guide rail on an axis corresponding to the determined direction. The X-ray apparatus may be easily moved based on force detection and velocity control of the motor, thereby achieving more precise and safe movement in a desired direction. Accordingly, the X-ray apparatus may provide rapid and efficient medical examination and treatment in hospitals.

17 Claims, 6 Drawing Sheets

X-RAY APPARATUS AND CONTROL METHOD THEREOF

CROSS-REFERENCE TO RELATED APPLICATIONS

This application claims the benefit of Korean Patent Application No. 2010-0098312, filed on Oct. 8, 2010 in the Korean Intellectual Property Office, the disclosure of which is incorporated herein by reference.

BACKGROUND

1. Field

Embodiments of the present disclosure relate to a multi-axis movable X-ray apparatus and a control method thereof.

2. Description of the Related Art

In the past, when a patient suffered internal injury or symptoms without a visible cause, doctors were forced to perform exploratory surgery to determine the extent of injury or the cause of the symptoms.

However, after Wilhelm Conrad Roentgen of Germany first developed X-rays, X-rays began to be employed for medical diagnosis. X-ray apparatuses are now used to non-invasively examine internal organs and bones, such as breast, head, digestive organs, and backbone, thereby serving as a facile diagnosis appliance.

X-rays are high-transmissivity electromagnetic waves emitted when matter is bombarded with fast electrons. An X-ray apparatus is designed such that an X-ray tube irradiates X-rays to an object, i.e. a target region of a human body placed between the X-ray tube and an X-ray film, thus imaging the target region via transmission of the X-rays.

The X-ray tube has 1~3 degrees of freedom suitable to photograph various regions of a human body. For example, the X-ray tube may be installed to the ceiling so as to be movable vertically and horizontally in all directions, and may be vertically and horizontally moved to a target position by an operator who grips a handle of the X-ray tube.

When using the above-described X-ray apparatus, however, the operator must inconveniently manually position the X-ray tube to center the X-ray tube on the X-ray film, and moreover, moving the heavy and bulky X-ray tube may be very difficult and requires considerable exertion.

To improve usability, an automated X-ray tube, a drive shaft of which is equipped with a motor to enable automated movement of the X-ray tube, has been developed.

To move the automated X-ray tube to a target position, the operator presses a button while confirming a moved position of the X-ray tube and then, turns off the button at the target position, or the X-ray tube may be moved to the target position through input of coordinates.

The above-described automated X-ray tube has no function to be fully aware of the surrounding environment during movement and thus, has difficulty moving fast in view of safety, thus slowing the rate at which patients may be examined using the X-ray apparatus.

In addition, the greater the degrees of freedom, operating buttons corresponding to the respective degrees of freedom may be more difficult and only less intuitive operation may be performed than manually moving the X-ray tube by directly gripping the handle of the X-ray tube.

SUMMARY

Aspects of the disclosure will be set forth in part in the description which follows and, in part, will be apparent from the description, or may be learned by practice of the disclosure.

In accordance with one aspect of the present disclosure, an X-ray apparatus includes a plurality of guide rails arranged along different axes, an X-ray tube mounted on at least one guide rail of the plurality of guide rails so as to be movable along a plurality of axes, the X-ray tube being moved upon receiving force applied by a user, motors provided respectively at the plurality of guide rails to provide the X-ray tube with moving force, a force detection unit to detect the user force applied to the X-ray tube, and a control unit to determine a direction of force if the force is detected, and drive the motor provided at the guide rail on an axis corresponding to the determined direction.

The X-ray apparatus may further include a velocity detection unit to detect a velocity of the motor, and the control unit may reduce the velocity of the motor if the detected velocity of the motor exceeds a preset reference velocity.

The control unit may reduce the velocity of the motor in proportion to a magnitude of the excess velocity if the detected velocity of the motor exceeds the reference velocity.

The control unit may determine a magnitude of force applied in each direction if the force is applied in a plurality of directions, and may drive the motor provided at the guide rail corresponding to a direction in which the greatest magnitude of force is applied while stopping the motor provided at the guide rail corresponding to the other direction.

The X-ray tube may include locks corresponding to the respective axes, and the control unit may drive the lock on the guide rail on an axis corresponding to the other direction.

The X-ray apparatus may further include an input unit to instruct movement of the X-ray tube along a single axis, and the control unit may determine a magnitude of force applied in each direction if an On signal is transmitted from the input unit, and may drive the motor provided at the guide rail corresponding to a direction in which the greatest magnitude of force is applied while stopping the motor provided at the guide rail corresponding to the other direction.

The X-ray tube may include a body to generate and output X-rays, and a handle to control a position of the body, and the force detection unit may be provided between the body and the handle.

The force detection unit may include a multi-axis load cell to detect a direction and magnitude of force along multiple axes.

The force detection unit may be provided in each direction of the handle corresponding to each axis.

The control unit may rotate the motor forward if the X-ray tube moves in a positive direction from a given position on a per axis basis and may rotate the motor in reverse if X-ray tube moves in a negative direction from the given position.

The motor provided at the guide rail on a per axis basis may include a first motor and a second motor, and the control unit may drive the first motor if the force is applied to move the X-ray tube in a positive direction from a given position and may drive the second motor if the force is applied to move the X-ray tube in a negative direction from the given position.

In accordance with another aspect of the present disclosure, an X-ray apparatus includes a guide rail, an X-ray tube movably mounted on the guide rail and adapted to be moved upon receiving force applied by a user, a motor provided at the guide rail to provide the X-ray tube with moving force during movement of the X-ray tube, a velocity detection unit to detect a velocity of the motor, and a control unit to compare the detected velocity of the motor with a preset reference velocity and reduce the velocity of the motor if the detected velocity of the motor exceeds the reference velocity.

The control unit may reduce the velocity of the motor in proportion to a magnitude of the excess velocity if the detected velocity of the motor exceeds the reference velocity.

The X-ray apparatus may further include a force detection unit to detect the user force applied to the X-ray tube, and the control unit may determine a direction of force if the force is detected, and may control a driving direction of the motor to correspond to the determined direction.

In accordance with another aspect of the present disclosure, an X-ray apparatus includes a guide rail, an X-ray detection unit movably mounted on the guide rail and adapted to be moved upon receiving force applied by a user, a motor provided at the guide rail to provide the X-ray detection unit with moving force during movement of the X-ray detection unit, a velocity detection unit to detect a velocity of the motor, a force detection unit to detect the user force applied to the X-ray detection unit, and a control unit to determine a direction of force if the force is detected and controls a driving direction of the motor to correspond to the determined direction, and to compare the detected velocity of the motor with a preset reference velocity during driving of the motor and reduce the velocity of the motor if the detected velocity of the motor exceeds the reference velocity.

The control unit may determine a magnitude of force and controls the velocity of the motor to correspond to the magnitude of force.

In accordance with another aspect of the present disclosure, a control method of an X-ray apparatus including a plurality of guide rails arranged along different axes and an X-ray tube mounted on at least one guide rail of the plurality of guide rails so as to be movable along a plurality of axes, includes determining whether or not force is applied to the X-ray tube, detecting the force if the force is applied to the X-ray tube, determining a direction of the force, and driving a motor provided at the guide rail on an axis corresponding to the determined direction under control.

The driving of the motor under control may include detecting a velocity of the motor during driving of the motor, comparing the detected velocity of the motor with a preset reference velocity, and reducing the velocity of the motor if the detected velocity of the motor exceeds the reference velocity.

The reduction of the velocity of the motor may include reducing the velocity of the motor in proportion to a magnitude of the excess velocity.

The driving of the motor under control may include determining a magnitude of the force, and controlling the velocity of the motor in proportion to the determined magnitude of the force.

The driving of the motor under control may include determining whether the force is applied in a plurality of directions, determining a magnitude of force applied in each direction if the force is applied in the plurality of directions, determining a direction in which the greatest magnitude of force is applied, driving the motor provided at the guide rail on an axis corresponding to the direction in which the greatest magnitude of force is applied, and stopping the motor provided at the guide rail on an axis corresponding to the other direction.

The control method may further include driving a lock provided at the guide rail on the axis corresponding to the other direction.

The control method may further include confirming an On/Off state of a button indicating single-axis movement of the X-ray tube, determining a magnitude of force applied in each direction if the button is in an On state, determining a direction in which the greatest magnitude of force is applied, driving the motor provided at the guide rail on an axis corresponding to the direction in which the greatest magnitude of force is applied, and stopping the motor provided at the guide rail on an axis corresponding to the other direction.

The driving of the motor provided at the guide rail on the axis corresponding to the determined direction under control may include rotating the motor forward if the determined direction of force corresponds to a direction to allow the X-ray tube to move in a positive direction from a given position, and rotating the motor in reverse if the determined direction of force corresponds to a direction to allow the X-ray tube to move in a negative direction from the given position.

In accordance with a further aspect of the present disclosure, a control method of an X-ray apparatus including a guide rail and an X-ray tube movably mounted on the guide rail and adapted to be moved upon receiving force applied by a user, includes determining whether or not force is applied to the X-ray tube, detecting the force if the force is applied to the X-ray tube, determining a direction of the force, driving a motor provided at the guide rail on an axis corresponding to the determined direction so as to provide the X-ray tube with moving force, detecting a velocity of the motor, comparing the detected velocity of the motor with a preset reference velocity during driving of the motor, and reducing the velocity of the motor if the detected velocity of the motor exceeds the reference velocity.

The driving of the motor provided at the guide rail on the axis corresponding to the determined direction may include controlling the velocity of the motor in proportion to a magnitude of the force.

The reduction of the velocity of the motor may include reducing the velocity of the motor in proportion to a magnitude of the excess velocity.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
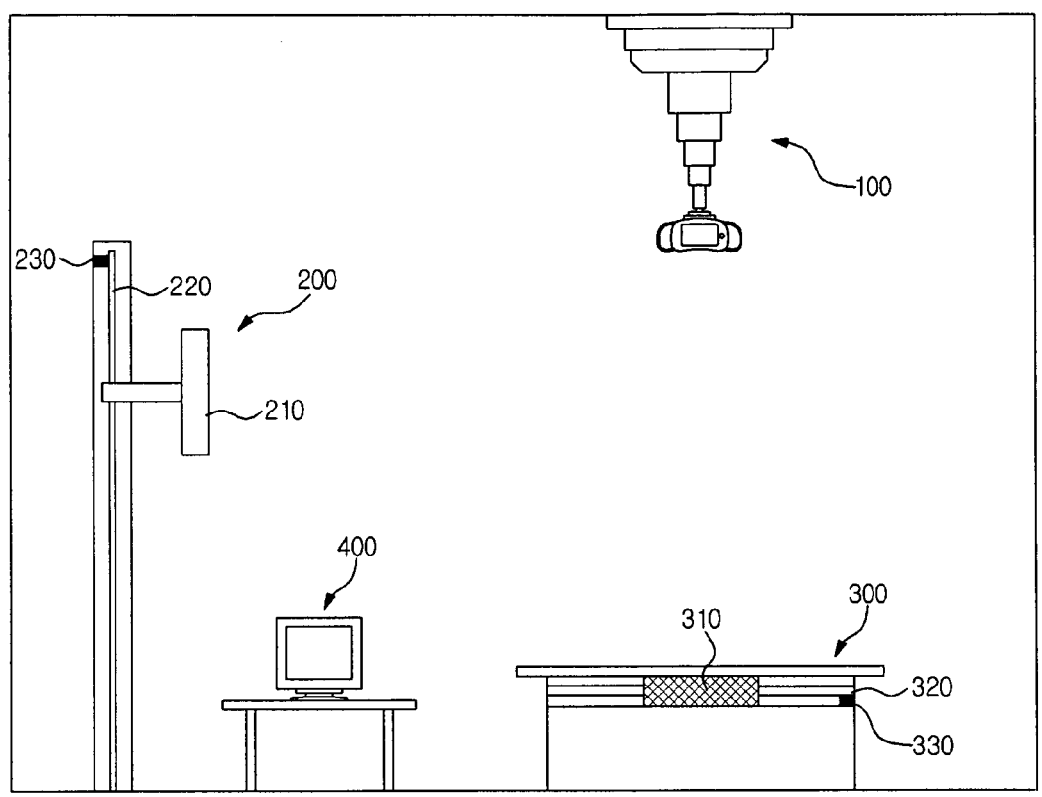
FIG. 1 is a view illustrating a configuration of an X-ray apparatus according to an embodiment of the present disclosure.

Reference will now be made in detail to the embodiments of the present disclosure, examples of which are illustrated in the accompanying drawings, wherein like reference numerals refer to like elements throughout.

FIG. 1 is a view illustrating a configuration of an X-ray apparatus according to an embodiment of the present disclosure.

The X-ray apparatus is a digital X-ray apparatus, which converts an X-ray image signal of a target object into a digital signal and then displays the converted digital signal containing the X-ray image of the object. The X-ray apparatus includes an X-ray generator 100, a first detector 200, a second detector 300, and a server 400.

The X-ray generator 100 emits X-rays using a predetermined high voltage and outputs the X-rays to the object.

Here, X-rays have a short wavelength, thus being highly energetic and easily passing through an object. Based on these characteristics, X-rays may be used to radiograph the interior of an object.

The X-ray generator 100 may be of a stand type or of a ceiling type, and have a plurality of degrees of freedom to move closer to the object. In the present embodiment, the ceiling type X-ray generator 100 will be described below with reference to FIGS. 3 to 6 by way of example.

The first detector 200 is of a stand type and detects X-rays having passed through an upright object and transmits the detected result to the server 400.

The first detector 200 includes an X-ray detection unit 210, a guide rail 220, and a motor 230.

The X-ray detection unit 210 is located to face an X-ray tube of the X-ray generator 100 with the upright object interposed therebetween, and detects an X-ray image of the object obtained when the X-rays output from the X-ray tube penetrate the object.

More specifically, if X-rays output from the X-ray tube of the X-ray generator 100 is introduced the X-ray detection unit 210 through a window of the X-ray detection unit 210, the X-ray detection unit 210 converts the X-rays into visible light using a fluorescent plate, thereby generating a visible image of the interior of the object.

With provision of the window through which the X-rays having passed through the object are introduced, the X-rays are incident upon the fluorescent plate. Thus, a front surface of the fluorescent plate senses a collision track of X-rays alone.

The X-ray detection unit 210 is provided with a toothed pinion, and in turn, the toothed pinion is connected to a motor 230 and is rotated by the motor 230.

The X-ray detection unit 210 is vertically movably mounted to the guide rail 220. The guide rail 220 guides movement of the X-ray detection unit 210 in a direction in which a user applies force.

The guide rail 220 is provided with a toothed rack, and in turn, the toothed rack is engaged with the pinion (not shown) of the X-ray detection unit 210. If the motor 230 is driven, the guide rail 220 guides movement of the X-ray detection unit 210 along the rack.

The motor 230 is connected to the pinion of the X-ray detection unit 210 and provides the pinion of the X-ray detection unit 210 with rotating force.

The motor 230 may be connected to the pinion of the X-ray detection unit 210 by use of a gear (not shown) or a wire (not shown).

Assuming that a shaft of the motor 230 is connected to a shaft of the pinion of the X-ray detection unit 210 by use of the gear, the motor 230 rotates the gear as the user moves the X-ray detection unit 210, thereby causing the pinion to be rotated and providing the X-ray detection unit 210 with additional moving force. Also, assuming that the shaft of the motor 230 is connected to the shaft of the pinion of the X-ray detection unit 210 by use of a wire, as the user moves the X-ray detection unit 210, the motor 230 is driven to cause the wire to be wound thereon or unwound therefrom, providing the X-ray detection unit 210 with additional moving force.

The second detector 300 takes the form of a table and detects X-rays having passed through the object placed on the table to transmit an X-ray image of the object to the server 400.

The second detector 300 includes an X-ray detection unit 310, a guide rail 320, and a motor 330.

The X-ray detection unit 310 is located to face an X-ray tube of the X-ray generator 100 with the object placed on a table interposed therebetween, and detects an X-ray image of the object obtained when the X-rays output from the X-ray tube penetrate the object.

More specifically, if X-rays output from the X-ray tube of the X-ray generator 100 is introduced the X-ray detection unit 310 through a window of the X-ray detection unit 310, the X-ray detection unit 310 converts the X-rays into visible light using a fluorescent plate, thereby generating a visible image of the interior of the object.

With provision of the window through which the X-rays having passed through the object are introduced, the X-rays are incident upon the fluorescent plate. Thus, a front surface of the fluorescent plate senses a collision track of X-rays alone.

The X-ray detection unit 310 is provided with a toothed pinion, and in turn, the toothed pinion is connected to a motor 330 and is rotated by the motor 330.

The X-ray detection unit 310 is horizontally movably mounted to the guide rail 320. The guide rail 320 guides movement of the X-ray detection unit 310 in a direction in which a user applies force.

The guide rail 320 is provided with a toothed rack, and in turn, the toothed rack is engaged with the pinion (not shown) of the X-ray detection unit 310. If the motor 330 is driven, the guide rail 320 guides movement of the X-ray detection unit 310 along the rack.

The motor 330 is connected to the pinion of the X-ray detection unit 310 and provides the pinion of the X-ray detection unit 310 with rotating force.

The motor 330 may be connected to the pinion of the X-ray detection unit 310 by use of a gear (not shown) or a wire (not shown).

Assuming that a shaft of the motor 330 is connected to a shaft of the pinion of the X-ray detection unit 310 by use of the gear, the motor 330 rotates the gear as the user moves the X-ray detection unit 310, thereby causing the pinion to be rotated and providing the X-ray detection unit 310 with additional moving force. Also, assuming that the shaft of the motor 330 is connected to the shaft of the pinion of the X-ray detection unit 310 by use of a wire, as the user moves the X-ray detection unit 310, the motor 330 is driven to cause the wire to be wound thereon or unwound therefrom, providing the X-ray detection unit 310 with additional moving force.

Figure 2:
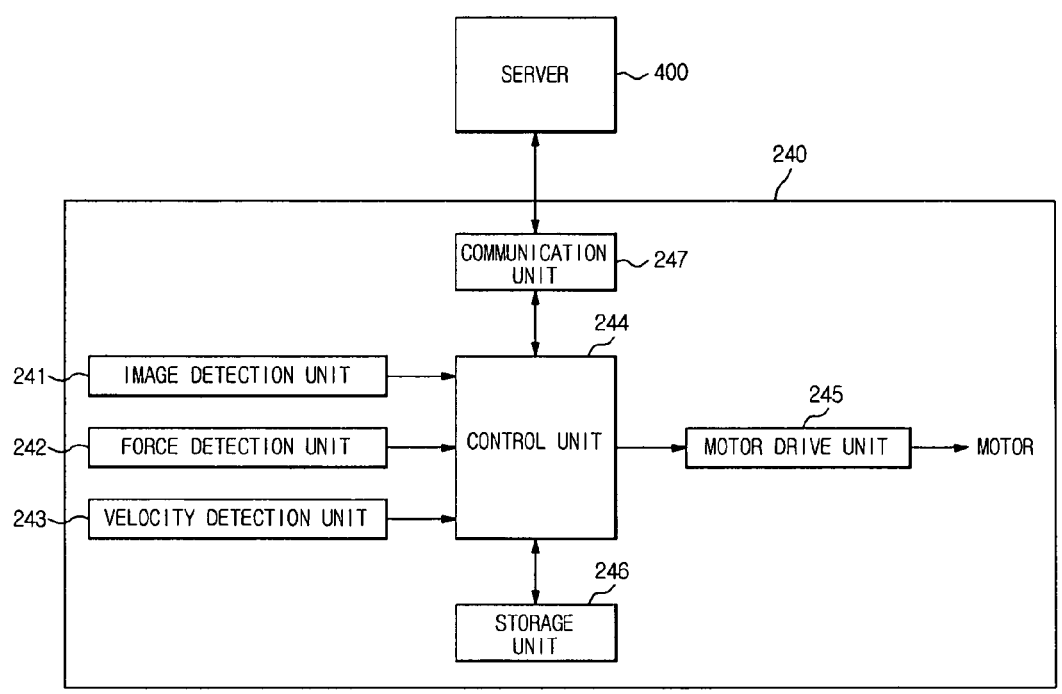
FIG. 2 is a control block diagram of a detector provided in the X-ray apparatus according to an embodiment of the present disclosure.

The control configuration of the first detector 200 and the second detector 300 will be described below with reference to FIG. 2. The first detector 200 and the second detector 300 have the same configuration and thus the first detector 200 will be described below by way of example.

A controller 240 of the first detector 200 includes an image detection unit 241, a force detection unit 242, a velocity detection unit 243, a control unit 244, a motor drive unit 245, a storage unit 246, and a communication unit 247.

The image detection unit 241 converts a visible X-ray image formed by the X-ray detection unit 210 into an electrical signal using an image sensor (e.g., CCD or CMOS), amplifies the converted analogue signal of the X-ray image to a predetermined level, converts the amplified analogue signal of the X-ray image into a digital signal, and processes and transmits the digital X-ray image signal to the server 400 through the communication unit 247.

In this case, visual spectrum light detected by the image sensor is very bright.

The force detection unit 242 is provided in the X-ray detection unit 210 and serves to detect user force applied to the X-ray detection unit 210 to transmit information of the detected force to the control unit 244.

The velocity detection unit 243 detects the velocity of the motor 230 during driving of the motor 230 and transmits the detected velocity information of the motor 230 to the control unit 244.

The control unit 244 determines a direction in which a user applies force and drives the motor 230 provided at the guide rail 210 on an axis corresponding to the determined direction so as to provide the X-ray tube with moving force.

The control unit 244 determines the magnitude of user force during driving of the motor 230, determines the velocity of the motor 230 in proportion to the determined magnitude of force, and drives the motor 230 at the determined velocity.

The control unit 244 compares the detected velocity of the motor 230 during driving of the motor 230 with a preset reference velocity, and reduces the velocity of the motor 230 if the detected velocity of the motor 230 exceeds the reference velocity. In this case, the control unit 244 determines a reduction rate of the velocity of the motor 230 in proportion to the magnitude of the excess velocity and drives the motor 230 at the determined reduced velocity.

Also, the control unit 244 drives the motor 230 forward if user force is applied in the current moving direction, and drives the motor 230 in reverse if user force is applied in an opposite direction of the current moving direction.

The motor drive unit 245 turns on or off the motor 230 in response to an instruction of the control unit 244, and drives the motor 230 to output a velocity corresponding to an instruction of the control unit 244.

The storage unit 246 stores information about the velocity of the motor 230 corresponding to the magnitude of force, the reduction rate of the velocity of the motor 230 corresponding to the magnitude of the excess velocity, and the reference velocity of the motor 230.

The communication unit 247 transmits the digital X-ray image signal to the server 400 in response to an instruction of the control unit 244.

The server 400 receives the X-ray image signal from at least one of the first detector 200 and the second detector 300.

If the server 400 receives a signal of an image printed on a film from the first detector 200 and the second detector 300, the server 400 converts the transmitted image signal into a digital signal and displays the converted digital X-ray image data.

In this case, information of the object is input to the server 400 to allow the server 400 to display and store the information along with the X-ray image data. Here, if the object is a person, personal information and inspection object and inspection item information are input to the server 400.

Figure 3:
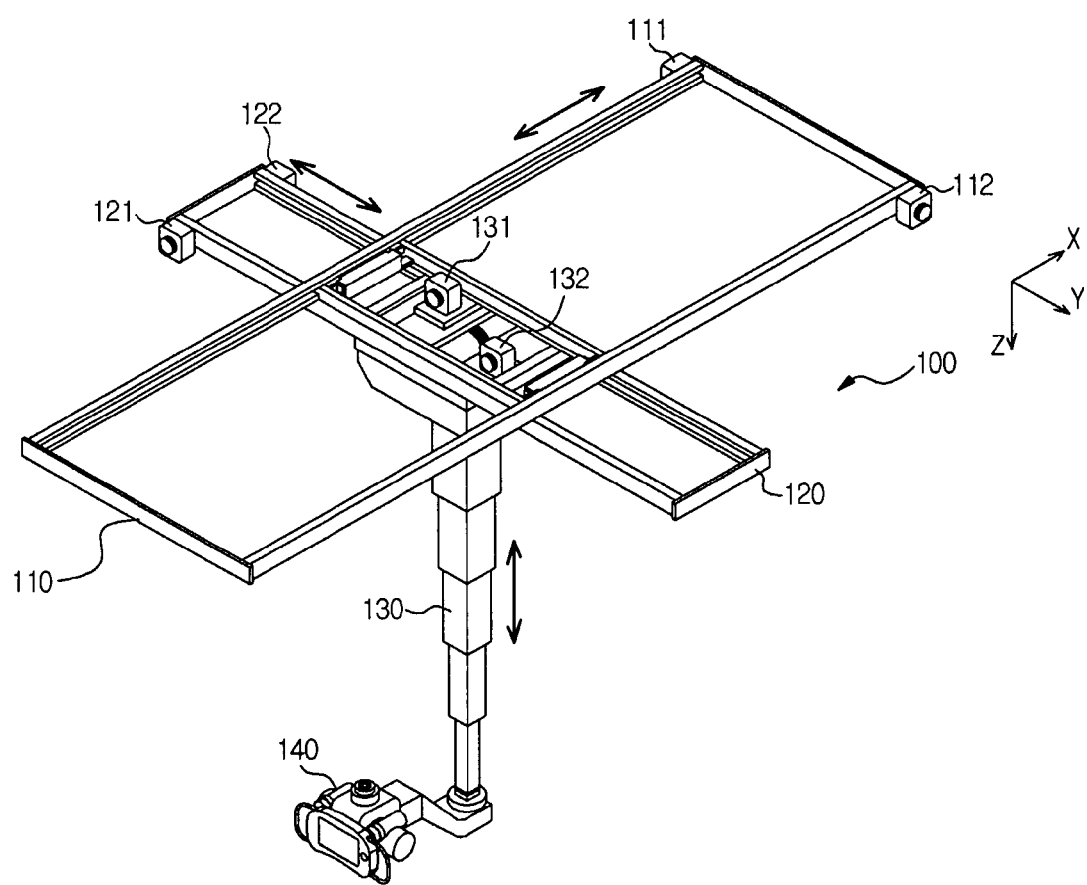
FIG. 3 is a view illustrating an installation example of an X-ray generator provided in the X-ray apparatus according to an embodiment of the present disclosure.
Figure 4:
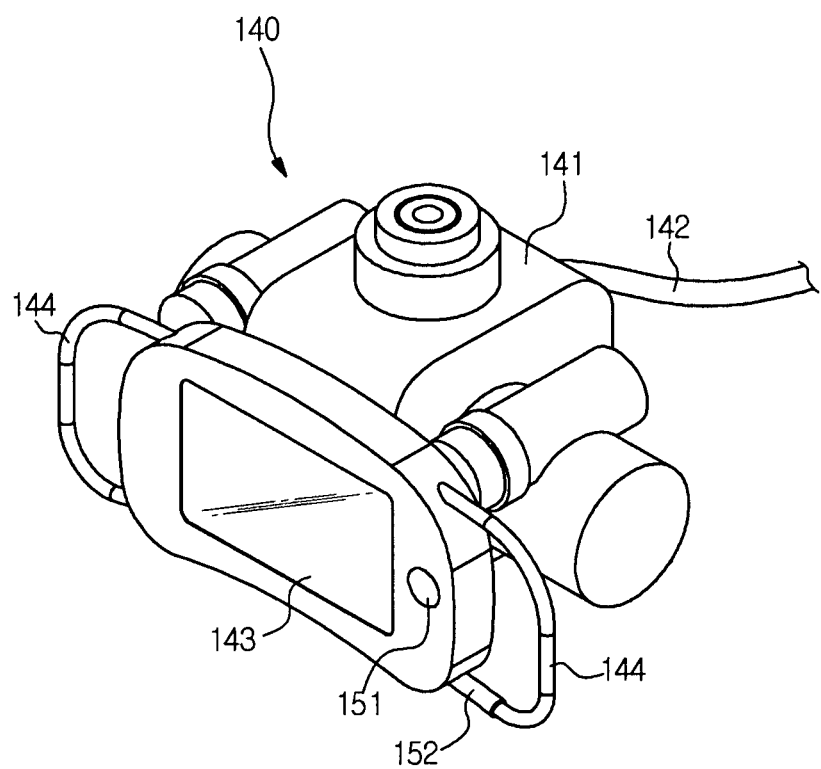
FIG. 4 is a view illustrating an X-ray tube provided in the X-ray apparatus according to an embodiment of the present disclosure.

FIG. 3 is a view illustrating an installation example of the X-ray generator provided in the X-ray apparatus according to an embodiment of the present disclosure, and FIG. 4 is a view illustrating the X-ray tube provided in the X-ray apparatus according to an embodiment of the present disclosure.

As illustrated in FIG. 3, the X-ray generator 100 is of the ceiling type having 3 degrees of freedom in X-, Y-, and Z-axes.

The X-ray generator 100 includes a first guide rail 110, a second guide rail 120, a third guide rail 130, and an X-ray tube 140. The first guide rail 110, the second guide rail 120 and the third guide rail 130 are stacked one above another. This configuration will be described below in detail by way of example.

The first guide rail 110 guides X-axis movement of the X-ray tube 140 if the user applies X-axis force to the X-ray tube 140.

The top of the first guide rail 110 is fixed to the ceiling and the bottom thereof is mounted on the second guide rail 120. The second guide rail 120 is movable along the X-axis.

The first guide rail 110 is provided with a toothed rack (not shown), and the toothed rack is engaged with a pinion (not shown) of the second guide rail 120.

The first guide rail 110 may be provided with one or more first motors 111 and 112. The first motors 111 and 112 provide the X-ray tube 140 with additional moving force while the user moves the X-ray tube 140 along the X-axis.

Each of the first motors 111 and 112 is connected to the pinion of the second guide rail 120 and provides the pinion of the second guide rail 120 with rotating force.

The first motors 111 and 112 may be connected to the pinion of the second guide rail 120 by use of a gear (not shown) or a wire (not shown).

More specifically, assuming that a shaft of each first motor 111 or 112 is connected to a shaft of the pinion of the second guide rail 120 by use of the gear, the first motor 111 or 112 rotates the gear as the user moves the X-ray tube 140, thereby causing the pinion of the second guide rail 120 to be rotated and providing the X-ray tube 140 with additional moving force. Also, assuming that the shaft of the first motor 111 or 112 is connected to the shaft of the pinion of the second guide rail 120 by use of a wire, as the user moves the X-ray tube 140, the first motor 111 or 112 is driven to cause the wire to be wound thereon or unwound therefrom, providing the X-ray tube 140 with additional moving force.

The first motors 111 and 112 are synchronously driven to facilitate X-axis movement of the X-ray tube 140. For example, the first motors 111 and 112 are rotated forward if the X-ray tube 140 moves in a positive direction (i.e. in a right direction) from a given position on the X-axis, and are rotated in reverse if the X-ray tube 140 moves in a negative direction (i.e. in a left direction) from the given position.

Alternatively, the first motors 111 and 112 may be alternately driven whenever the direction in which a user applies force is changed. For example, the first motor 111 is rotated forward if the X-ray tube 140 moves in a positive direction from the given position, and the first motor 112 is rotated in reverse if the X-ray tube 140 moves in a negative direction from the given position.

That is, the first guide rail 110 guides X-axis movement of the X-ray tube 140 along the rack when the first motors 111 and 112 are driven.

The second guide rail 120 guides Y-axis movement of the X-ray tube 140 if user applies force in the Y-axis to the X-ray tube 140. The second guide rail 120 is perpendicular to the first guide rail 110.

The top of the second guide rail 120 is mounted to the first guide rail 110 to enable X-axis movement of the second guide rail 120, and the bottom thereof is mounted to the third guide rail 130 to enable Y-axis movement of the third guide rail 130.

Specifically, the top of the second guide rail 120 is provided with the pinion (not shown) to be engaged with the rack of the first guide rail 110, and the bottom thereof is provided with a toothed rack (not shown) to be engaged with a pinion (not shown) of the third guide rail 130.

The second guide rail 120 may be provided with one or more second motors 121 and 122. The second motors 121 and 122 provide the X-ray tube 140 with additional moving force while the user moves the X-ray tube 140 along the Y-axis.

Each of the second motors 121 and 122 is connected to the pinion of the third guide rail 130 and provides the pinion of the third guide rail 130 with rotating force.

The second motors 121 and 122 may be connected to the pinion of the third guide rail 130 by use of a gear (not shown) or a wire (not shown).

More specifically, assuming that a shaft of each second motor 121 or 122 is connected to a shaft of the pinion of the third guide rail 130 by use of the gear, the second motor 121 or 122 rotates the gear as the user moves the X-ray tube 140, thereby causing the pinion of the third guide rail 130 to be rotated and providing the X-ray tube 140 with additional moving force. Also, assuming that the shaft of the second motor 121 or 122 is connected to the shaft of the pinion of the third guide rail 130 by use of a wire, as the user moves the X-ray tube 140, the second motor 121 or 122 is driven to cause the wire to be wound thereon or unwound therefrom, providing the X-ray tube 140 with additional moving force.

The second motors 121 and 122 are synchronously driven to facilitate Y-axis movement of the X-ray tube 140. For example, the second motors 121 and 122 are rotated forward if the X-ray tube 140 moves in a positive direction (i.e. in a right direction) from a given position on the Y-axis, and are rotated in reverse if the X-ray tube 140 moves in a negative direction (i.e. in a left direction) from the given position.

Alternatively, the second motors 121 and 122 may be alternately driven whenever the direction in which a user applies force is changed. For example, the second motor 111 is rotated forward if the X-ray tube 140 moves in a positive direction from the given position and the second motor 122 is rotated in reverse if the X-ray tube 140 moves in a negative direction from the given position.

That is, the second guide rail 120 guides Y-axis movement of the X-ray tube 140 along the rack when the second motors 121 and 122 are driven.

The third guide rail 130 guides Z-axis movement of the X-ray tube 140 if user applies force in the Z-axis to the X-ray tube 140. The third guide rail 130 is installed in a normal direction of the first guide rail 110 and the second guide rail 120.

The third guide rail 130 includes a plurality of telescopic frames.

The top of the third guide rail 130 is mounted to the second guide rail 120 to enable Y-axis movement of the third guide rail 130, and the bottom thereof is provided with the X-ray tube 140 to enable Z-axis movement of the X-ray tube 140.

Specifically, the top of the third guide rail 130 is provided with an upper pinion (not shown) to be engaged with the rack of the second guide rail 120. In addition, the third guide rail 130 is internally provided with a toothed vertical rack (not shown) and a pinion (not shown) to be engaged with the toothed rack.

The third guide rail 130 may be provided with one or more third motors 131 and 132. The third motors 131 and 132 provide the X-ray tube 140 with additional moving force while the user moves the X-ray tube 140 along the Z-axis.

Each of the third motors 131 and 132 is connected to the inner pinion of the third guide rail 130 and provides the pinion of the third guide rail 130 with rotating force.

The third motors 131 and 132 may be connected to the inner pinion of the third guide rail 130 by use of a gear (not shown) or a wire (not shown).

More specifically, assuming that a shaft of each third motor 131 or 132 is connected to a shaft of the inner pinion by use of the gear, the third motor 131 or 132 rotates the gear as the user moves the X-ray tube 140, thereby causing the inner pinion to be rotated and providing the X-ray tube 140 with additional moving force. Also, assuming that the shaft of the third motor 131 or 132 is connected to the shaft of the inner pinion by use of a wire, as the user moves the X-ray tube 140, the third motor 131 or 132 is driven to cause the wire to be wound thereon or unwound therefrom, providing the X-ray tube 140 with additional moving force.

The third motors 131 and 132 are synchronously driven to facilitate Z-axis movement of the X-ray tube 140. For example, the third motors 131 and 132 are rotated forward if the X-ray tube 140 moves in a positive direction (i.e. in a right direction) from a given position on the Z-axis, and are rotated in reverse if the X-ray tube 140 moves in a negative direction (i.e. in a left direction) from the given position.

Alternatively, the third motors 131 and 132 may be alternately driven whenever the direction in which a user applies force is changed. In this case, the third motor 131 is rotated forward if the X-ray tube 140 moves in a positive direction from the given position and the third motor 132 is rotated in reverse if the X-ray tube 140 moves in a negative direction from the given position.

That is, the third guide rail 130 guides Z-axis movement of the X-ray tube 140 along the rack when the third motors 131 and 132 are driven.

The third guide rail 130 is provided with a first lock corresponding to the X-axis, a second lock corresponding to the Y-axis, and a third lock corresponding to the Z-axis. If the user wants to move the X-ray tube 140 only along a single axis, the locks corresponding to the other axes are driven to prevent movement of the X-ray tube 140 along the other axes.

If user force and drive force of the motor 130 are applied to the X-ray tube 140, the X-ray tube 140 is moved on at least one of the first guide rail 110, the second guide rail 120 and the third guide rail 130 so as to be located near the object and outputs X-rays according to user instruction.

In operation of the X-ray tube 140, if a high voltage is applied between a cathode and an anode, thermal electrons generated from the cathode filament collide with the metallic anode, thereby generating X-rays via collision with electrons in the metallic anode.

The interior of the X-ray tube 140 is kept at vacuum to reduce loss of dynamic energy and deflection caused when electrons collide with molecules while being blown to a target. The target is made of a thin metal film and the thickness of the target is determined in consideration of the penetration depth of electrons and the absorption of heat generated from the target.

X-ray tubes may be classified into stationary X-ray tubes and rotary X-ray tubes according to the operating manner of the anode. The rotary X-ray tubes have approximately the same function as the stationary X-ray tubes except that the anode is rotated to disperse heat generated from the target.

Thereby, actually, the X-ray tube moves toward the cathode when measuring a thick region of the object and moves toward the anode when measuring a thin region of the object.

The X-ray tube 140 includes a body 141, a tube 142, an X-ray generation unit 143, and handles 144. The X-ray tube 140 is further provided with an input unit 151 and a force detection unit 152.

The body 141 defines an external appearance of the X-ray tube 140, and protects a variety of components to generate X-rays.

The tube 142 applies a high voltage between the anode and the cathode.

The X-ray generation unit 143 generates X-rays via collision between thermal electrons generated from the cathode filament and electrons in the metallic anode, and outputs the X-rays to the object.

The handles 144 are mounted to the body 141 to enable manual operation.

The input unit 151 includes a button indicating single-axis movement of the X-ray tube 140, is turned on or off by the user, and transmits a manual operation signal to the control unit 154.

The force detection unit 152 is provided between the body 141 and each of the handles 144. The force detection unit 152 detects user force applied to the handle 144, and may include a multi-axis load cell to detect multi-axis force.

The force detection unit 152 detects the magnitude of force and the directivity of force on a per axis basis, i.e. whether force is applied in a positive direction or a negative direction from the given position.

Alternatively, the force detection unit 152 may include single-axis load cells respectively corresponding to a plurality of axes.

Figure 5:
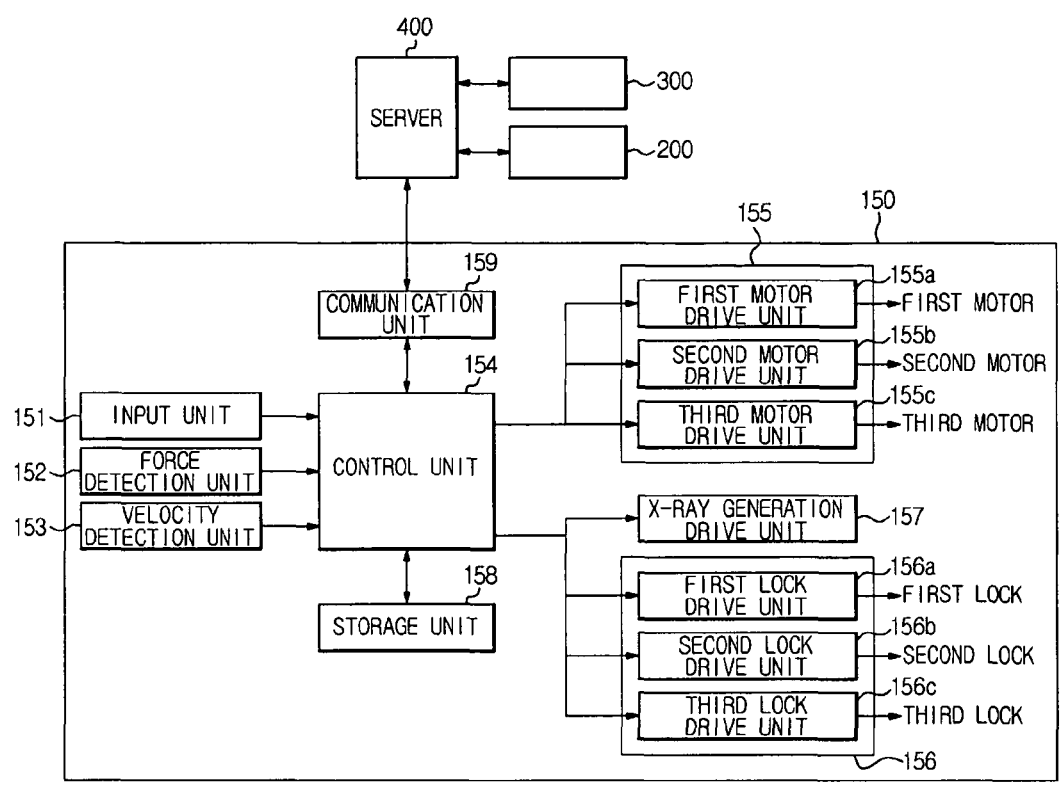
FIG. 5 is a control block diagram of the X-ray generator provided in the X-ray apparatus according to an embodiment of the present disclosure.

FIG. 5 is a control block diagram of the X-ray generator provided in the X-ray apparatus according to an embodiment of the present disclosure.

A controller 150 provided in the X-ray generator 110 of the X-ray apparatus includes the input unit 151, the force detection unit 152, a velocity detection unit 153, the control unit 154, a motor drive unit 155, a lock drive unit 156, an X-ray generator drive unit 157, a storage unit 158, and a communication unit 159.

The input unit 151 includes a button indicating single-axis movement of the X-ray tube 140, is turned on or off by the user, and transmits a manual operation signal to the control unit 154.

The input unit 151 is provided because it may be necessary to move the X-ray tube 140 only along a single-axis rather than moving in all directions according to operation environment or as necessary.

The force detection unit 152 detects user force applied to the handle 144 along a plurality of axes (i.e. X-, Y-, and Z-axes) and transmits the detected result to the control unit 154.

The force detection unit 152 includes a multi-axis load cell, which detects multi-axis force and outputs an electrical signal.

The multi-axis load cell is a combination of plural load cells and is designed to measure physical force, i.e. torque simultaneously.

The multi-axis load cell is a force sensor to simultaneously detect three-axis force and three-axis moment acting on a load point.

The multi-axis load cell has a very complex configuration required to provide appropriate force detecting elements corresponding to force and moment in several directions within a single elastic body. In particular, the multi-axis load cell used to detect force may be designed to have high accuracy and precision and low volume and weight as well as high strength to minimize positional error.

Alternatively, the force detection unit 152 may include single-axis load cells respectively corresponding to a plurality of axes.

The single-axis load cells are installed in a plurality of axes (i.e. X-, Y-, and Z-axes) between the body 141 and the handle 144, and serve to detect compressive force and tensile force applied thereto and transmit the detected compressive force and tensile force to the control unit 154. The control unit 154 determines the magnitude and direction of force based on the compressive force and tensile force of each single-axis load cell.

The velocity detection unit 153 detects the velocity of the motor provided at each of the guide rails 110, 120 and 130. The velocity detection unit 153 may be provided to correspond to the motor of each of the guide rails 110, 120 and 130. Here, the velocity detection unit 153 may be an encoder.

The control unit 154 determines the direction of user force when applied, and drives the motor provided at the guide rail on an axis corresponding to the determined direction.

In this case, the control unit 154 determines the magnitude of user force and controls the motor to drive at a velocity corresponding to the determined magnitude of force.

For example, the control unit 154 rotates the motor forward if the X-ray tube 140 moves in a positive direction from the given position and rotates the motor in reverse if the X-ray tube moves in a negative direction from the given position.

If two motors per axis are alternately driven, the control unit 154 drives one of the motors if the X-ray tube 140 moves in a positive direction from the given position and drives the other motor if the X-ray tube 140 moves in a negative direction from the given position.

Here, the positive direction corresponds to a rightward direction on the X-axis, a forward direction on the Y-axis, and an upward direction on the Z-axis, and the negative direction corresponds to a leftward direction on the X-axis, a rearward direction on the Y-axis, and a downward direction on the Z-axis.

The control unit 154 reduces the velocity of the motor if the detected velocity of the motor exceeds a preset reference velocity. Specifically, if the detected velocity of the motor exceeds the preset reference velocity, the motor reduces the velocity of the motor in proportion to the magnitude of the excess velocity.

If the detected velocity of the motor exceeds the preset reference velocity, resistance against a movement direction occurs, preventing the heavy X-ray tube 140 from moving excessively rapidly and resulting in safe use of the X-ray tube 140.

If an On signal is transmitted from the input unit 151, the control unit 154 determines the magnitude of force applied in each direction. Then, the control unit 154 drives the motor of the guide rail corresponding to a direction in which the greatest force is applied while stopping the motors of the other guide rails corresponding to the other directions and simultaneously, drives the locks of the other guide rails.

In this way, if the user wants to move the X-ray tube only in a single axis direction, the user may restrict movement in other directions except for a desired direction by moving the X-ray tube while pushing the button of the handle of the X-ray tube.

Assuming that the force detection unit 152 includes a plurality of single-axis load cells, the control unit 154 may be provided at each of left, right, and lower (or upper) positions of the handle to determine the direction and magnitude of force based on the compressive force and tensile force detected by the respective load cells.

For example, if the left handle 144 is pushed and the right handle 144 is pulled such that compressive force is applied to a left load cell and tensile force is applied to a right load cell, the motor provided at the X-axis guide rail 110 is rotated forward. On the other hand, if the left handle 144 is pulled and the right handle 144 is pushed such that compressive force is applied to the right load cell and tensile force is applied to the left load cell, the motor provided at the X-axis guide rail 110 is rotated in reverse.

If the handles 144 are pushed forward to apply compressive force to the left and right load cells, the motor provided at the Y-axis guide rail 120 is rotated forward. On the other hand, if the handles 144 are pushed rearward to apply tensile force to the left and right load cells, the motor provided at the Y-axis guide rail 120 is rotated in reverse.

If the handles 144 are pushed upward to apply compressive force to lower load cells, the motor provided at the Z-axis guide rail 130 is rotated forward. On the other hand, if the handles 144 are pushed downward to apply tensile force to the lower load cells, the motor provided at the Z-axis guide rail 130 is rotated in reverse.

Assuming that force is applied in plural directions, the control unit 154 determines the magnitude of force applied in each direction. Then, the control unit 154 drives the motor of the guide rail corresponding to a direction in which the greatest force is applied while stopping the motors of the other guide rails corresponding to the other directions and simultaneously, drives the locks of the other guide rails.

The motor drive unit 155 includes a first motor drive unit 155*a*, which drives the first motors 111 and 112 provided at the first guide rail 110 corresponding to the X-axis in response to an instruction of the control unit 154, a second motor drive unit 155*b*, which drives the second motors 121 and 122 provided at the second guide rail 120 corresponding to the Y-axis in response to an instruction of the control unit 154, and a third motor drive unit 155*c*, which drives the third motors 131 and 132 provided at the third guide rail 130 corresponding to the Z-axis in response to an instruction of the control unit 154.

The lock drive unit 156 includes a first lock drive unit 156*a*, which drives a first lock to stop movement of the X-ray tube 140 on the first guide rail 110 corresponding to the X-axis in response to an instruction of the control unit 154, a second lock drive unit 156*b*, which drives a second lock to stop movement of the X-ray tube 140 on the second guide rail 120 corresponding to the Y-axis in response to an instruction of the control unit 154, and a third lock drive unit 156*c*, which drives a third lock to stop movement of the X-ray tube 140 on the third guide rail 130 corresponding to the Z-axis in response to an instruction of the control unit 154.

The X-ray generator drive unit 157 allows the X-ray generation unit 143 to generate X-rays in response to an instruction of the control unit 157.

The storage unit 158 stores a reference velocity, information about the velocity of the motors 111, 112, 121, 122, 131 and 132 corresponding to the magnitude of force, and a reduction rate in the velocity of the motor 230 in proportion to the magnitude of the excess velocity.

The communication unit 159 transmits an X-ray generation instruction signal received from the server 400 to the control unit 154.

As described above, by providing the X-ray tube of the X-ray apparatus with additional force using the force detection unit and the motor when the user moves the X-ray apparatus with gripping the handle of the X-ray tube, more easy movement of the X-ray tube may be accomplished.

That is, intuitive movement of the X-ray tube may be accomplished even with low force as result of mixing advantages of automatic operation and manual operation.

Figure 6:
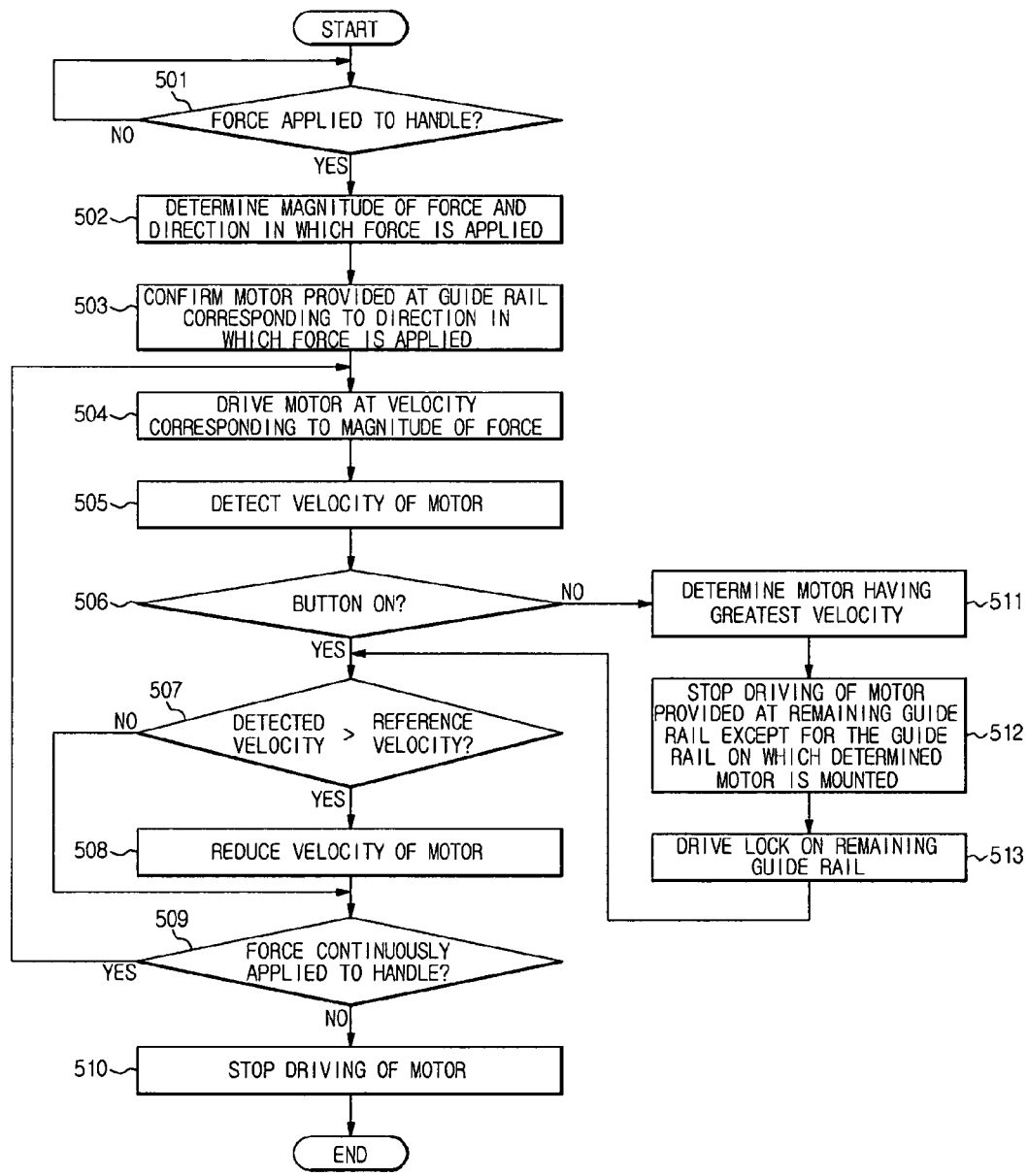
FIG. 6 is a control flow chart of the X-ray generator provided in the X-ray apparatus according to an embodiment of the present disclosure.

FIG. 6 is a control flow chart of the X-ray generator provided in the X-ray apparatus according to an embodiment of the present disclosure. The control operation of the X-ray generator will be described below with reference to FIGS. 3 to 5.

First, the force detection unit 152 determines whether or not force is applied to the handle 144 provided at the body 141 of the X-ray tube 140 (501).

If a patient is located near the detector 200 or 300, the user applies force to the handle 144 of the X-ray tube 140 of the X-ray generator 100. If the force is applied to the handle 144, the force detection unit 152 detects the direction and magnitude of force (502). Here, the force is applied in at least one of X-, Y- and Z-axes.

Next, the motor provided at the guide rail corresponding to the axis in which the force is applied is confirmed (503), and the motor is driven at a velocity corresponding to the magnitude of force (504).

If force is applied in plural directions, the velocity of the motor provided at the guide rail of the axis corresponding to each direction is determined according to the magnitude of force corresponding to each direction. In this case, the velocity of the motor is proportional to the magnitude of force.

Specifically, if the user grips and pushes the handle 144, the motor corresponding to the direction in which the user applies force is rotated to assist the user, causing the X-ray tube 140 of the X-ray generator 100 to move along at least one guide rail.

The velocity detection unit 153 detects the velocity of the motor (505), and it is determined whether or not the user pushes the button of the input unit 151 (506).

If the button is in an off-state, the detected velocity of the motor during driving of the motor is compared with a preset reference velocity (507). If the detected velocity exceeds the reference velocity, the velocity of the motor is reduced (508).

Next, it is determined whether force is continuously applied to the handle (509). If no force is applied to the handle 144, it is determined that the X-ray tube 140 of the X-ray generator 100 reaches a target position, i.e. the object and thus, the motor is stopped (510). If force is continuously applied to the handle 144, the motor is driven at a velocity corresponding to the magnitude of force.

On the other hand, if the button of the input unit 151 is in an on-state, it is determined which one of the motors has the greatest velocity (511), and the motors provided at the other guide rails except for the guide rail on which the determined motor is mounted are stopped (512). Simultaneously, the locks of the other guide rails are driven to prevent the X-ray generator 100 from moving along the other guide rails (513).

Next, the detected velocity of the single motor that is being driven is compared with a preset reference velocity (507). If the detected velocity exceeds the reference velocity, the velocity of the motor is reduced (508).

Next, it is determined whether force is continuously applied to the handle 144 (509). If no force is applied to the handle 144, it is determined that the X-ray tube 140 of the X-ray generator 100 reaches a target position and thus, the motor is stopped (510).

If force is continuously applied to the handle 144, only the motor determined in operation 511 is driven.

If the X-ray tube 140 of the X-ray generator 100 reaches the target position to face the detector 200 or 300 with the object, i.e. the patient interposed therebetween, the user instructs generation of X-rays.

Thereby, the X-ray tube 140 of the X-ray generator 100 generates X-rays, and the detector 200 or 300 detects an X-ray image.

Next, the detector 200 or 300 transmits the detected image to the server 400, and the server 400 displays the transmitted X-ray image.

In this case, the server 400 displays and stores personal information and other important information concerning the object, i.e. the patient.

As is apparent from the above description, according to the embodiment of the present disclosure, an X-ray apparatus may be easily moved based on force detection and motor velocity control, thereby achieving more precise and safe movement in a desired direction.

Accordingly, the X-ray apparatus according to the embodiment of the present disclosure may provide rapid and efficient medical examination and treatment in hospitals.

Although a few embodiments of the present disclosure have been shown and described, it would be appreciated by those skilled in the art that changes may be made in these embodiments without departing from the principles and spirit of the invention, the scope of which is defined in the claims and their equivalents.

What is claimed is:

1. An X-ray apparatus comprising:
a plurality of guide rails arranged along different axes;
an X-ray tube mounted on at least one guide rail of the plurality of guide rails so as to be movable along a plurality of axes, the X-ray tube being moved upon receiving force applied by a user;
motors provided respectively at the plurality of guide rails to provide the X-ray tube with moving force;
a force detection unit to detect the user force applied to the X-ray tube; and
a control unit to determine a direction of force if the force is detected, and drive the motor provided at the guide rail on an axis corresponding to the determined direction,
wherein the control unit determines a magnitude of force applied in each direction if the force is applied in a plurality of directions, and drives the motor provided at the guide rail corresponding to a direction in which the greatest magnitude of force is applied while stopping the motor provided at the guide rail corresponding to the other direction.

2. The apparatus according to claim 1, further comprising a velocity detection unit to detect a velocity of the motor,
wherein the control unit reduces the velocity of the motor if the detected velocity of the motor exceeds a preset reference velocity.

3. The apparatus according to claim 2, wherein the control unit reduces the velocity of the motor in proportion to a magnitude of the excess velocity if the detected velocity of the motor exceeds the reference velocity.

4. The apparatus according to claim 1, wherein the X-ray tube includes locks corresponding to the respective axes, and the control unit drives the lock on the guide rail on an axis corresponding to the other direction.

5. The apparatus according to claim 1, wherein the control unit rotates the motor forward if the X-ray tube moves in a positive direction from a given position on a per axis basis and rotates the motor in reverse if X-ray tube moves in a negative direction from the given position.

6. The apparatus according to claim 1, wherein:
the motor provided at the guide rail on a per axis basis includes a first motor and a second motor; and
the control unit drives the first motor if the force is applied to move the X-ray tube in a positive direction from a given position and drives the second motor if the force is applied to move the X-ray tube in a negative direction from the given position.

7. An X-ray apparatus comprising:
a plurality of guide rails arranged along different axes;
an X-ray tube mounted on at least one guide rail of the plurality of guide rails so as to be movable along a plurality of axes, the X-ray tube being moved upon receiving force applied by a user;
motors provided respectively at the plurality of guide rails to provide the X-ray tube with moving force;
a force detection unit to detect the user force applied to the X-ray tube;
a control unit to determine a direction of force if the force is detected, and drive the motor provided at the guide rail on an axis corresponding to the determined direction; and
an input unit to instruct movement of the X-ray tube along a single axis,
wherein the control unit determines a magnitude of force applied in each direction if an On signal is transmitted from the input unit, and drives the motor provided at the guide rail corresponding to a direction in which the greatest magnitude of force is applied while stopping the motor provided at the guide rail corresponding to the other direction.

8. The apparatus according to claim 7, wherein:
the X-ray tube includes a body to generate and output X-rays, and a handle to control a position of the body; and
the force detection unit is provided between the body and the handle.

9. The apparatus according to claim 8, wherein the force detection unit includes a multi-axis load cell to detect a direction and magnitude of force along multiple axes.

10. The apparatus according to claim 8, wherein the force detection unit is provided in each direction of the handle corresponding to each axis.

11. A control method of an X-ray apparatus comprising a plurality of guide rails arranged along different axes and an X-ray tube mounted on at least one guide rail of the plurality of guide rails so as to be movable along a plurality of axes, the method comprising:
determining whether or not force is applied to the X-ray tube;
detecting the force if the force is applied to the X-ray tube;
determining a direction of the force; and
driving a motor provided at the guide rail on an axis corresponding to the determined direction under control,
wherein the driving of the motor under control includes
determining whether the force is applied in a plurality of directions;
determining a magnitude of force applied in each direction if the force is applied in the plurality of directions;
determining a direction in which the greatest magnitude of force is applied;
driving the motor provided at the guide rail on an axis corresponding to the direction in which the greatest magnitude of force is applied; and
stopping the motor provided at the guide rail on an axis corresponding to the other direction.

12. The method according to claim 11, wherein the driving of the motor under control includes:
detecting a velocity of the motor during driving of the motor;
comparing the detected velocity of the motor with a preset reference velocity; and
reducing the velocity of the motor if the detected velocity of the motor exceeds the reference velocity.

13. The method according to claim 12, wherein the reduction of the velocity of the motor includes reducing the velocity of the motor in proportion to a magnitude of the excess velocity.

14. The method according to claim 11, wherein the driving of the motor under control includes:
determining a magnitude of the force; and
controlling the velocity of the motor in proportion to the determined magnitude of the force.

15. The method according to claim 11, further comprising driving a lock provided at the guide rail on the axis corresponding to the other direction.

16. The method according to claim 11, wherein the driving of the motor provided at the guide rail on the axis corresponding to the determined direction under control includes:
   rotating the motor forward if the determined direction of force corresponds to a direction to allow the X-ray tube to move in a positive direction from a given position; and
   rotating the motor in reverse if the determined direction of force corresponds to a direction to allow the X-ray tube to move in a negative direction from the given position.

17. A control method of an X-ray apparatus comprising a plurality of guide rails arranged along different axes and an X-ray tube mounted on at least one guide rail of the plurality of guide rails so as to be movable along a plurality of axes, the method comprising:
   determining whether or not force is applied to the X-ray tube;
   detecting the force if the force is applied to the X-ray tube;
   determining a direction of the force;
   driving a motor provided at the guide rail on an axis corresponding to the determined direction under control;
   confirming an On/Off state of a button indicating single-axis movement of the X-ray tube;
   determining a magnitude of force applied in each direction if the button is in an On state;
   determining a direction in which the greatest magnitude of force is applied;
   driving the motor provided at the guide rail on an axis corresponding to the direction in which the greatest magnitude of force is applied; and
   stopping the motor provided at the guide rail on an axis corresponding to the other direction.

* * * * *